(12) United States Patent
Eikje

(10) Patent No.: US 10,801,952 B2
(45) Date of Patent: Oct. 13, 2020

(54) SKIN CANCER BIOMARKER DETECTION BY INFRARED SPECTROSCOPY

(71) Applicants: MC PROFFESIONAL LTD., Tallinn (EE); IR CLINICAL CANCER DIAGNOSTICS LTD., Oslo (NO); Natalja Eikje, Oslo (NO)

(72) Inventor: Natalja Eikje, Oslo (NO)

(*) Notice: Subject to any disclaimer, the term of this patent is extended or adjusted under 35 U.S.C. 154(b) by 223 days.

(21) Appl. No.: 14/387,517

(22) PCT Filed: Mar. 23, 2013

(86) PCT No.: PCT/EE2013/000003
§ 371 (c)(1),
(2) Date: Sep. 4, 2019

(87) PCT Pub. No.: WO2013/139348
PCT Pub. Date: Sep. 26, 2013

(65) Prior Publication Data
US 2019/0310187 A1    Oct. 10, 2019

Related U.S. Application Data

(60) Provisional application No. 61/651,498, filed on May 24, 2012, provisional application No. 61/612,294, filed on Apr. 10, 2012.

(51) Int. Cl.
*G01N 21/3563* (2014.01)
*A61B 5/00* (2006.01)
*G01N 33/483* (2006.01)
*G01N 21/35* (2014.01)

(52) U.S. Cl.
CPC ....... *G01N 21/3563* (2013.01); *A61B 5/0075* (2013.01); *A61B 5/444* (2013.01); *G01N 21/35* (2013.01); *G01N 33/4833* (2013.01); *G01N 2021/3595* (2013.01)

(58) Field of Classification Search
CPC ............... A61B 5/0071; A61B 5/444; G01N 2021/3595; G01N 21/3563; G01N 33/4833
See application file for complete search history.

(56) References Cited

U.S. PATENT DOCUMENTS

| 9,572,494 | B2 | 2/2017 | Dhawan | |
|---|---|---|---|---|
| 2012/0259229 | A1* | 10/2012 | Wang | G01N 21/65 600/476 |
| 2014/0058224 | A1* | 2/2014 | Gellermann | G01N 21/3563 600/314 |

FOREIGN PATENT DOCUMENTS

| AU | 2013236860 B2 | 3/2018 |
|---|---|---|
| CN | 1890557 A | 1/2007 |
| CN | 109307657 A | 2/2019 |
| EP | 2241245 A1 | 10/2010 |
| JP | 2019113555 A | 7/2019 |
| KR | 20080043843 A | 5/2008 |
| WO | 2013139348 A1 | 9/2013 |

OTHER PUBLICATIONS

Eikje Natalja Skrebova Ed—Kollias Nikiforos et al: "DNA-RNA, DNA-DNA, DNA-protein and protein-protein interactions in diagnosis of skin cancers by FT-IR micro spectroscopy", Photon IC Therapeutics and Diagnostics VII, SPIE, 1000 20th St. Bellingham WA 98225-6705 USA, vol. 7883, No. 1, Feb. 10, 2011 (Feb. 10, 2011), pp. 1-5, XP060006072.
Eikje N S: "Numerical modeling and analytical treatment of IR spectra in the diagnosis of skin cancers", Proceedings of SPIE, SPIE—International Society for Optical Engineering, Bellingham, WA, US, vol. 7999, Oct. 22, 2010 (Oct. 22, 2010), pp. 1-6, XP002698177.
Eikje N S: "Vibrational spectroscopy for molecular characterisation and diagnosis of benign, premalignant and malignant skin tumours", Biotchnology Annual Review, vol. 11, ISSN: 1387-2656, Oct. 7, 2005 (Oct. 7, 2005), pp. 191-225.
Natalja Skrebova Eikje: "Potential of lasers and optical technologies for clinical applications in dermatology /title", Proceedings of SPIE, vol. 6163, Aug. 1, 2006 (Aug. 1, 2006), pp. 616309-616309-16, XP55067 434.
WIPO, International Search Report for PCT international patent application serial No. PCT/EE2013/00003, dated Sep. 23, 2013, 3 pages.
WIPO, Written Opinion of the International Searching Authority for PCT international patent application serial No. PCT/EE2013/00003, dated Sep. 23, 2013, 9 pages.
WIPO, International Preliminary Report on Patentability for PCT international patent application serial No. PCT/EE2013/00003, dated Sep. 23, 2014, 10 pages.
IP Australia, Notice of Acceptance for Australian patent application serial No. AU2013236860A, dated Feb. 14, 2018, 38 pages.
IP Australia, Amendment for Australian patent serial No. AU2013236860A, dated Jan. 25, 2018, 163 pages.
IP Australia, Examination Report 6 for Australian patent serial No. AU2013236860A, dated Jan. 25, 2018, 4 pages.
IP Australia, Examination Report 5 for Australian patent serial No. AU2013236860A, dated Jan. 22, 2018, 6 pages.
IP Australia, Amendment for Australian patent serial No. AU2013236860A, dated Jan. 15, 2018, 79 pages.
IP Australia, Examination Report 4 for Australian patent serial No. AU2013236860A, dated Jan. 4, 2018, 7 pages.

(Continued)

*Primary Examiner* — David P Porta
*Assistant Examiner* — Fani Boosalis
(74) *Attorney, Agent, or Firm* — D'Hue Law LLC; Cedric A. D'Hue

(57) ABSTRACT

The present invention relates to a method for detection in IR (infrared) spectra of human epidermal skin tissue the presence of the multiplet around 1055 $cm^{-1}$, i.e. the ratio of intensity of the nucleic acids bands, DNA and RNA, indicative for prognosis, diagnosis and prediction of epidermal skin cancers and precancers. Detection of the multiplet together with patterned appearance of DNA/RNA triad peaks at about 1071, 1084/1085 and 1095 $cm^{-1}$ additionally indicates relation to certain types of tumour and malignancy, also indicating progression of malignancy and progression towards malignancy.

15 Claims, No Drawings

(56) References Cited

OTHER PUBLICATIONS

IP Australia, Amendment for Australian patent serial No. AU2013236860A, dated Dec. 21, 2017, 111 pages.
IP Australia, Examination Report 3 for Australian patent serial No. AU2013236860A, dated Aug. 15, 2017, 8 pages.
IP Australia, Amendment for Australian patent serial No. AU2013236860A, dated Jul. 11, 2017, 99 pages.
IP Australia, Examination Report 2 for Australian patent serial No. AU2013236860A, dated May 19, 2017, 5 pages.
IP Australia, Amendment for Australian patent serial No. AU2013236860A, dated Mar. 7, 2017, 34 pages.
IP Australia, Examination Report 1 for Australian patent serial No. AU2013236860A, dated Jan. 27, 2017, 6 pages.

* cited by examiner

SKIN CANCER BIOMARKER DETECTION BY INFRARED SPECTROSCOPY

BACKGROUND OF THE INVENTION

1. Field of the Invention

This invention pertains in general to the field of identification of a molecular cancer biomarker in human skin epidermal cancerous tissue from a biopsy through IR (infrared) spectral assignment of the multiplet at around 1055 cm$^{-1}$. More specifically, this involves the detection method, IR spectroscopy, to identify the presence of DNA/RNA ratio peak in human epidermis, diagnostic for squamous cell carcinoma (SCC), basal cell carcinoma (BCC) and malignant melanoma (MM). The specificity and sensitivity of skin cancer biomarker band is correlated with skin cancer type and its progression, towards determination of prognosis and prediction of the treatment in the patient. Qualitative and quantitative assessment of a molecular cancer biomarker in human skin epidermal cancerous tissue all together indicate prognosis, diagnosis and prediction of epidermal skin cancers and precancers. Detection of the multiplet together with patterned appearance of DNA/RNA triad peaks at about 1071, 1084/1085 and 1095 cm$^{-1}$ additionally indicates relation to certain types of tumour and malignancy, also indicating progression of malignancy and progression towards malignancy.

Although skin tissue is used as the representative tissue, the detection method for a biomarker is not limited to measuring skin epidermal tissue and can be exploited with other tissues, as will be apparent to the skilled person.

2. Prior Art

The specificity and sensitivity of clinical diagnosis of epidermal skin cancers varies from approximately 40 to 80%. The diagnostic accuracy depends largely on the length of training and experience of the clinician: reported to be 80% for trained dermatologists, 62% for senior registars, 56% for registars and approximately 40% for non-dermatologists. So, clinical diagnostic accuracy of basal cell carcinoma (BCC), the most common cancer of the skin, is only 65% for practising dermatologists. Another skin cancer, derived from the middle part of the epidermis, squamous cell carcinoma (SCC), is easily diagnosed in typical clinical cases, but may sometimes difficult to diagnose when located on the genitalia and lips, leading to misdiagnosis and rapid metastasizing, with death resulting in about 75% of the patients. Precancerous dermatoses, such as Bowen's disease (intraepidermal carcinoma in situ) and many others, are often difficult to diagnose in a dermatology clinic, because many other skin lesions mimic them. Clinical diagnosis of malignant melanoma (MM) can be often confused with benign pigmented lesions, resulting in up to 80% of unnecessary biopsies. Importantly, patients with diagnosis of MM should be monitored for the rest of their lives and examined for local recurrence, metastasis and fresh malignant lesions.

Dermoscopy has been reported to improve the diagnostic accuracy of epidermal skin cancers and precancers, based on numerous features for establishing morphological pattern recognition. Nevertheless, recognition of these patterns requires a long training in dermatology, and still interpretation of numerous cases vary largely between the experts.

Confocal microscopy might be useful in the diagnosis of epidermal skin cancers and precancers, based on interpretion of cellular images of keratinocytes in the epidermis, based again on cellular morphological recognition of pathology-related patterns in conjunction with correlation to standard histology. Although this technique increases the diagnostic accuracy of epidermal skin cancers and precancers, there have been described limitations for certain skin lesions.

Conventional histopathological identification of cancerous tissues from a biopsy by morphological pattern recognition remains gold standard for clinical diagnosis of skin tumours, though the major drawbacks of the histopathological assessment are delays in diagnosis and interpretational variations among the pathologists.

In order to reduce false-negative results, an increasing requirement has been felt for a new and complimentary diagnostic technique to improve the diagnostic potential of "difficult to determine cases" in a shorter time-frame. Thus, there is an urgent need in clinical dermatology today for novel, rapid, non-invasive diagnostic techniques, that can be applied for real-time primary and follow-up screening to compliment a clinical diagnosis of skin tumours, ideally replacing human interpretation.

Infrared (IR) microspectroscopy is a tool for spectroscopic evaluation of unstained tissues from biopsies at any anatomical location. Allowing easy visualization of cellular components based on their intrinsic properties and chemical composition without a requirement of external contrast-inducing agents, this technique provides sample-specific molecular information, unique spectral fingerprints for molecules of nucleic acids, proteins, lipids, water, thus providing a potential route to obtain diagnostic markers for diseases.

Spectroscopic analysis of cancerous tissues has received considerable attention to be a diagnostic technique due to its sensitivity to biochemical variations in the samples from a variety of human cancers.

Skin tissue IR absorbance spectrum fits all the characteristics for a development of a clinically useful biomarker. Proteins, the most abundant species in cells, dominate in the observed spectra of cells and tissues, including skin, because their consistence in those is about 60%. Nucleic acids in IR spectra from benign, premalignant and malignant skin cancers have been always observed in the presence of proteins. The nucleic acids DNA and RNA are especially important, because they carry within their structure hereditary information that determines the identity and structure of proteins. The mid-IR absorbance spectrum is one of the most information-rich and concise way to represent the whole proteomics of a cell, because of its high sensitivity to the conformation of nucleic acids and their conformational transitions, identification of base composition, its sensitivity to the effect of base-pairing interactions and base-stacking effects, etc. This makes IR spectroscopy technique more advantageous over another vibrational spectroscopy technique, Raman spectroscopy, that only provides information related to individual nucleotides.

Recent reports demonstrate FT (Fourier transform) IR spectroscopy as a potentially powerful analytical method with a high sensitivity, based on the results to identify the spectral changes of biological activity in cancerous cells in culture before appeared morphological changes, to commonly and specifically characterize skin carcinogenesis in human skin tumours based on analysis of intra- and inter-molecular interactions for nucleic acids and proteins expressed in IR spectra from benign, premalignant and malignant skin lesions.

Due to these methodological advantages, it is a purpose of this invention to determine and validate consistent and significant spectral parameters (biomarkers), which can evidently discriminate between normal (healthy, unchanged) and cancerous cells in human skin tissues, useful for prognosis, diagnosis and prediction of epidermal skin cancers and precancers.

Verification and validation of skin cancer biomarker band in IR spectra from human skin tissue might have further impact on determination of the most effective therapy in each patient and even determination of the most effective dosage of drug, aiding the field of personalized medicine.

SUMMARY OF THE INVENTION

The invention presents methods of using FTIR microspectroscopy for detecting the multiplet at about 1055 cm$^{-1}$, whose presence and increased expression in epidermal skin tissue is indicative for diagnosis and follow-up of epidermal skin cancers and precancers. The invented method is based on identification of the ratio of intensity of two bands of nucleic acids, DNA and RNA, in IR spectra of biopsied cancerous skin tissue samples. More particularly, provided detection method of a biomarker is a fast and reagent-free method for qualitative and quantitative analysis of identified multiplet at about 1055 cm$^{-1}$ in epidermal cancerous skin tissues, that is not detected in normal epidermal skin tissue. Detection of the multiplet together with patterned appearance of DNA/RNA triad peaks at about 1071, 1084/1085 and 1095 cm$^{-1}$ additionally indicates relation to certain types of tumour and malignancy, also indicating progression of malignancy and progression towards malignancy.

The method can be carried out manually and comprises of the following steps:
  obtaining FTIR spectra from a multitude of histopathologically proven pathological sites in epidermis on a sample, ideally from a whole pathology area
  possibly, obtaining control measurements throughout unchanged, healthy epidermis, for spectral comparison with pathological sites within each sample of the individual
  normalizing each of the spectrum to amide I peak (1650 cm$^{-1}$)
  averaging all epidermal measurements to obtain an average for the sample
  if identifiable, an assignment of the multiplet at about 1055 cm$^{-1}$ in the specified region for nucleic acids between 900 and 1300 cm$^{-1}$ In the above method, the biopsied tissue samples with established histopathological diagnosis are prepared for measurements by using FTIR microspectroscopy by the following steps:
  strictly sequential 2 sample cuts having a thickness of 6 micrometers
  staining 1 sample cut with hematoxilin and eosin for histopathological evaluation
  air-drying 1 sample cut on CaF$_2$ slide glass for collection of FTIR spectra All the above and other characteristics and advantages of the invention will be further described.

DETAILED DESCRIPTION OF THE INVENTION

The method of the invention will now be described in more detail.

FTIR microspectrometer by JEOL Co. Ltd. (Tokyo, Japan), a model IR-MAU200, has been used for IR spectral acquisition from skin tissue samples. Before each measurement, a calibration was performed using a sample provided with the instrument by the manufacturer, and proper operating conditions of FTIR microspectrometer was confirmed.

The tissue samples used for FTIR microspectroscopy measurements were in the dry state, while the corresponding slides observed by light microscope were stained with hematoxilin and eosin for the identification of pathology-related tissue structure.

Initially, the background spectrum was collected. After the measurement site was chosen by using the visible light, the microscope was changed to IR mode. The number of co-added scans were increased to 127 in order to achieve high signal-to-noise ratio. The aperture size used in the measurements was 25×25 micrometers. The measured spectra at a resolution of 4 cm$^{-1}$ covered the wavenumber range between 800 and 4000 cm$^{-1}$.

Spectral preprocessing methods applied to all measured FTIR spectra have included:
  if necessary, spike removal and smoothing, in order to reduce the high frequency instrumental noise
  baseline correction, in order to eliminate the dissimilarities between spectra due to shifts in baseline
  the amide I normalization at about 1650 cm$^{-1}$, due to its high sensitivity to small changes in molecular conformation and hydrogen bonding of peptide groups
  pick peaks assignment in the 900-1700 cm$^{-1}$ region.

The invention method included the following steps for detecting the ratio of intensity of two bands for nucleic acids, DNA and RNA, in the multiplet around 1055 cm$^{-1}$ in epidermal skin cancerous tissues:
  assignment of the multiplet at around 1055 cm$^{-1}$
  calculation of mean value of assigned multiplet at around 1055 cm$^{-1}$
  calculation of the intensity ratio $I_{1055}/I_{1245}$ Data used in the examples below derive from histopathologically confirmed tissue specimens from the biopsy archive of the Department of Dermatology, Tokushima University, Tokushima, Japan.

Together, the data employed in the skin cancerous tissue samples were extracted from 24 subjects.

A database of having measured 87 spectra from 13 patients with epidermal skin cancers, including 6 patients with BCC, 4 patients with SCC and 3 patients with MM, in comparison to a database of 21 measured spectra from normal epidermis in 4 healthy subjects.

In examples there were also used a database of having measured 80 spectra from 3 patients with Bowen's disease, a precancerous dermatosis, and a database of having measured 80 spectra from 4 patients with melanocytic nevi, benign compound type.

EXAMPLES

Tables 1-7 is a summary of data employed from the patients with BCC, SCC, MM, Bowen's disease and melanocytic nevus.

Detection of the Multiplet in Epidermal Skin Cancers

Skin cancer biomarker, the multiplet expressed by the level of the peak at about 1055 cm$^{-1}$, has been significant in all measured epidermal skin cancers—BCC, SCC and MM, since there was no appearance of this peak in normal skin tissue epidermis. Mean intensities of the peak at about 1055 cm$^{-1}$ has varied from 0.09 to 0.47 in BCC; from 0.13 to 0.66 in SCC; from 0.14 to 0.26 in MM patients, thus differing as low, medium and high within their variation ranges.

Example 1

Basal Cell Carcinoma (BCC)

Table 1 summarizes IR spectral detection of a biomarker band by means of analysis of mean values of the multiplet at about 1055 cm$^{-1}$ with variations, mean intensity ratio ($I_{1055}/I_{1245}$) with variations and mean peak position at about 1055 cm$^{-1}$ with variations in 6 patients with BCC.

| Patients with BCC | No. of spectra | Mean value (variation) | $I_{1055}/I_{1245}$ (variation) | Mean peak position (variation) |
|---|---|---|---|---|
| patient 1 | 10 spectra | 0.47 (0.40-0.59) | 0.96 (0.93-0.98) | 1060 cm$^{-1}$ (1059-1061) |
| patient 2 | 10 spectra | 0.43 (0.31-0.45) | 0.95 (0.94-0.96) | 1060 cm$^{-1}$ (1055-1067) |
| patient 3 | 5 spectra | 0.44 (0.27-0.59) | 0.94 (0.84-0.98) | 1058 cm$^{-1}$ (1052-1064) |
| patient 4 | 10 spectra | 0.19 (0.13-0.26) | 0.87 (0.50-1.00) | 1055 cm$^{-1}$ (1051-1061) |
| patient 5 | 9 spectra | 0.14 (0.12-0.18) | 0.67 (0.63-0.86) | 1053 cm$^{-1}$ (1047-1062) |
| patient 6 | 8 spectra | 0.09 (0.07-0.13) | 0.59 (0.54-0.63) | 1061 cm$^{-1}$ (1057-1063) |

In the presented 52 spectra from 6 patients with BCC the intensity of a biomarker band by the intensity ratio $I_{1055}/I_{1245}$ has varied between 0.59 and 0.96.

Right-shifted mean peak position of the multiplet has been observed in 4 patients independently from the level of intensity of a biomarker. Nevertheless, right-shifted variations for mean peak position of a biomarker has been seen in all patients with BCC.

Example 2

Squamous Cell Carcinoma (SCC)

Table 1 summarizes IR spectral detection of a biomarker band by means of analysis of mean values of the multiplet at about 1055 cm$^{-1}$ with variations, mean intensity ration ($I_{1055}/I_{1245}$) with variations and mean peak position at about 1055 cm$^{-1}$ with variations in 4 patients with SCC.

| Patients with SCC | No. of spectra | Mean value (variation) | $I_{1055}/I_{1245}$ (variation) | Mean peak position (variation) |
|---|---|---|---|---|
| patient 1 | 5 spectra | 0.66 | 1.00 | 1060 cm$^{-1}$ |
| patient 2 | 3 spectra | 0.30 (0.26-0.34) | 0.81 (0.74-0.94) | 1054 cm$^{-1}$ (1049-1058) |
| patient 3 | 9 spectra | 0.13 (0.07-0.25) | 0.77 (0.50-1.04) | 1059 cm$^{-1}$ (1056-1064) |
| patient 4 | 3 spectra | x | x | x |

In the presented 20 spectra from 4 patients with SCC the intensity of a biomarker band by the intensity ratio $I_{1055}/I_{1245}$ has been presented only in 3 patients with SCC and varied between 0.77 and 1.00.

Right-shifted variations for mean peak position of the multiplet at about 1055 cm$^{-1}$ has been seen in 3 patients with SCC, but right-shifted mean peak position has been detected in 2 patients with SCC with different intensity levels.

Example 3

Malignant Melanoma (MM)

Table 3 summarizes IR spectral detection of a biomarker band by means of analysis of mean values of the multiplet at about 1055 cm$^{-1}$ with variations, mean intensity ratio ($I_{1055}/I_{1245}$) with variations and mean peak position at about 1055 cm$^{-1}$ with variations in 3 patients with MM.

| Patients with MM | No. of spectra | Mean value (variation) | $I_{1055}/I_{1245}$ (variation) | Mean peak position (variation) |
|---|---|---|---|---|
| patient 1 | 4 spectra | 0.26 (0.26-0.27) | 0.69 (0.68-0.71) | 1054 cm$^{-1}$ (1052-1056) |
| patient 2 | 7 spectra | 0.14 (0.13-0.15) | 0.47 (0.43-0.50) | 1050 cm$^{-1}$ (1043-1064) |
| patient 3 | 4 spectra | x | x | x |

In 11 spectra obtained in the epidermis of 2 patients with MM the intensity of a biomarker band by the intensity ratio $I_{1055}/I_{1245}$ has varied between 0.47 and 0.69.

Left-shifted mean peak position of the multiplet detectable in 2 patients with MM, have showed large variations between 1043 and 1064 cm$^{-1}$.

Example 4

BCC vs. SCC vs. MM vs. Healthy Epidermis

Table 4 summarizes IR spectral detection of a biomarker band by means of analysis of mean values of the multiplet at about 1055 cm$^{-1}$ with variations, mean intensity ratio ($I_{1055}/I_{1245}$) with variations and mean peak position at about 1055 cm$^{-1}$ with variations in all measured patients with epidermal skin cancers (BCC, SCC. MM) vs. healthy subjects.

| Subjects | No. of patients | No. of spectra | Mean value (variation) | $I_{1055}/I_{1245}$ (variation) | Mean peak position (variation) |
|---|---|---|---|---|---|
| Healthy | 4 | 21 spectra | x | x | x |
| BCC | 6 | 52 spectra | 0.30 (0.09-0.44) | 0.83 (0.59-0.96) | 1058 cm$^{-1}$ (1053-1062) |
| SCC | 3 | 17 spectra | 0.36 (0.13-0.66) | 0.86 (0.77-1.00) | 1057 cm$^{-1}$ (1054-1060) |
| MM | 2 | 11 spectra | 0.20 (0.14-0.26) | 0.58 (0.47-0.69) | 1052 cm$^{-1}$ (1043-1064) |

Significant mean values of a biomarker band at about 1055 cm$^{-1}$ has been calculated as 0.20 for MM, 0.30 for BCC and 0.36 for SCC, in comparison with no peak appearance in healthy epidermis.

The intensity of a biomarker band by the intensity ratio $I_{1055}/I_{1245}$ was 0.58 for MM, with similar to each other, 0.83 for BCC and 0.86 for SCC.

Right-shifted mean peak position of a biomarker band was similar in 6 patients with BCC and in 3 patients with SCC, accordingly at 1057 cm$^{-1}$ and 1058 cm$^{-1}$. Largely variated left-shifted mean peak position of a biomarker band in 2 patients with MM was detected at 1052 cm$^{-1}$.

Detection of the Multiplet in Epidermal Precancers

A precancerous dermatosis, Bowen's disease, is the earliest form of skin cancer, so-called carcinoma in situ. Untreated cases are reported to progress into invasive carcinoma.

Example 1

Bowen's Disease

Table 1 summarizes IR spectral detection a biomarker band by means of analysis of mean values of the multiplet at about 1055 cm$^{-1}$ with variations, mean intensity ratio ($I_{1055}/I_{1245}$) with variations and mean peak position at about 1055 cm$^{-1}$ with variations in 3 patients with Bowen's disease.

| Patients with BD | Total No. of spectra | No. of spectra with the multiplet | Mean value (variation) | $I_{1055}/I_{1245}$ (variation) | Mean peak position (variation) |
|---|---|---|---|---|---|
| patient 1 | 10 spectra | x | x | x | x |
| patient 2 | 24 spectra | 3 spectra | 0.15 (0.13-0.16) | 0.66 (0.63-0.69) | 1053 cm$^{-1}$ (1051-1056) |
| patient 3 | 36 spectra | 10 spectra | 0.26 (0.22-0.29) | 0.77 (0.63-1.00) | 1052 cm$^{-1}$ (1050-1057) |

In epidermally measured 70 spectra in 3 patients with Bowen's disease, only 13 spectra in 2 patients selectively detected the appearance of a biomarker band, the multiplet at about 1055 cm$^{-1}$.

So, in one patient with histopathologically proven Bowen's disease, mean value of a biomarker band calculated on the basis of three IR spectra was 0.15, with small variations between 0.13 and 0.16. The intensity of a biomarker band by the intensity ratio $I_{1055}/I_{1245}$ was 0.66, varying between 0.63 and 0.69. Left-positioned mean peak at 1053 cm$^{-1}$ has varied between 1051 and 1056 cm$^{-1}$.

In another histopathologically proven patient with Bowen's disease, mean value of a biomarker band calculated on the basis of ten IR spectra was 0.26 with the range between 0.22 and 0.29. The intensity of a biomarker band by the intensity ratio $I_{1055}/I_{1245}$ was 0.77, varying between 0.63 and 1.00. Similar to other measured patient, left-positioned mean peak at 1052 cm$^{-1}$ has varied between 1050 and 1057 cm$^{-1}$.

Example 2

Bowen's Disease vs. SCC vs. Healthy Epidermis

Table 2 summarizes IR spectral detection of a biomarker band by means of analysis of mean values of the multiplet at about 1055 cm$^{-1}$ with variations, mean intensity ratio ($I_{1055}/I_{1245}$) with variations and mean peak position at about 1055 cm$^{-1}$ with variations in all measured patients with SCC, Bowen's disease vs. healthy subjects.

| All subjects | Total No. of spectra | No. of spectra with 1055 cm$^{-1}$ | Mean value (variation) | $I_{1055}/I_{1245}$ (variation) | Mean peak position (variation) |
|---|---|---|---|---|---|
| 4 healthy | 21 | 21 spectra in 4 subjects | x | x | x |
| 3 BD | 70 | 13 spectra in 2 patients | 0.21 (0.15-0.26) | 0.72 (0.66-0.81) | 1053 cm$^{-1}$ (1052-1053) |
| 3 SCC | 20 | 17 spectra in 2 patients | 0.36 (0.13-0.66) | 0.86 (0.77-1.00) | 1057 cm$^{-1}$ (1054-1060) |

Detected biomarker band was not constant and prominent at the appearance in IR spectra measured in the patients with Bowen's disease (only in 13 spectra of 2 patients out of 70 spectra of 3 patients), in comparison to SCC (in all spectra measured in 2 patients among 3 patients with SCC). Mean value of a biomarker for Bowen's disease was 0.21 with a variation between 0.15 and 0.26, but mean value of a biomarker for SCC was 0.36 with a variation between 0.13 and 0.66.

The intensity of a biomarker band by the intensity ratio $I_{1055}/I_{1245}$ was lower in Bowen's disease, mean calculated as 0.72 with a variation between 0.66 and 0.81, in comparison to SCC mean calculated intensity of a biomarker as 0.86, with a variation between 0.77 and 1.00.

It is obvious detection of a left-shifted position of mean peak at 1053 cm$^{-1}$ in the patients with Bowen's disease, compared to a right-shifted position of mean peak at 1057 cm$^{-1}$ in the patients with SCC.

Detection of the Multiplet in Melanocytic Nevus

Histopathologically, nevus cells (melanocytes) are normally localized in the basal layer of the epidermis. Their proliferation may appear in the epidermis (junctional nevus), in the epidermis and dermis (compound nevus) or only in the dermis (intradermal nevus). All types of nevi are melanocytic (nevocellular, melanocellular), benign nevi.

Therefore, there were used histopathologically confirmed samples of compound nevi for comparative epidermal acquisition of IR spectra of benign melanocytic nevi in 4 patients

Example 1

Table 1 summarizes IR spectral detection of a biomarker band by means of analysis of mean values of the multiplet at about 1055 cm$^{-1}$ with variations, mean intensity ratio ($I_{1055}/I_{1245}$) and mean peak position at about 1055 cm$^{-1}$ with variations in 4 patients with benign melanocytic nevi, compound nevus type.

| Patients with MN | Total No. of measured spectra | No. of spectra with 1055 cm$^{-1}$ | Mean value (variation) | $I_{1055}/I_{1245}$ (variation) | Mean peak position (variation) |
|---|---|---|---|---|---|
| patient 1 | 12 | 5 | 0.22 (0.15-0.31) | 0.71 | 1055 cm$^{-1}$ (1051-1055) |
| patient 2 | 10 | 10 | 0.19 (0.08-0.33) | 0.59 | 1054 cm$^{-1}$ (1052-1058) |
| patient 3 | 8 | 2 | 0.24 | 0.75 | 1055 cm$^{-1}$ |
| patient 4 | 18 | 9 | 0.17 (0.09-0.25) | 0.68 | 1053 cm$^{-1}$ (1051-1058) |

A biomarker band at about 1055 cm$^{-1}$ has been detected in all measured patients with melanocytic nevus, a compound type nevus, but not constantly. In the epidermis, a biomarker band has been detected in 26 spectra out of totally obtained 48 spectra in 4 patients with melanocytic nevus: in 5 out of 12 measured spectra in Patient 1, in all 10 measured spectra in Patient 2, in 2 spectra out of 8 measured spectra in Patient 3, and in 9 spectra out of 18 measured spectra in Patient 4.

Mean values for detected biomarker have varied between 0.17 and 0.24 in 4 patients with melanocytic nevus.

Mean intensities of detected biomarker band by the intensity band ratio $I_{1055}/I_{1245}$ ranged within 0.59-0.75 among patients with melanocytic nevi.

In the patients with melanocellular nevi mean peak position for a biomarker has been determined between 1053 and 1055 cm$^{-1}$, thus with left-shifted position.

Example 2

MM vs. MN vs. Healthy Epidermis

Table 2 summarizes IR spectral detection of a biomarker by means of analysis of mean values of the multiplet at about 1055 cm$^{-1}$ with variations, mean intensity ratio ($I_{1055}/I_{1245}$) with variations and mean peak position at about 1055 cm$^{-1}$ with variations in all measured patients with MM, melanocytic nevus (MN) (benign compound nevus) vs. healthy subjects.

| Subjects | Total No. of spectra | No. of spectra with multiplet | Mean value (variation) | $I_{1055}/I_{1245}$ (variation) | Mean peak position (variation) |
|---|---|---|---|---|---|
| 4 healthy | 21 | 21 spectra in 4 subjects | x | x | x |
| 4 MN | 48 | 26 spectra in 4 patients | 0.20 (0.17-0.24) | 0.68 (0.59-0.75) | 1054 cm$^{-1}$ (1053-1055) |
| 3 MM | 15 | 11 spectra in 2 patients | 0.20 (0.14-0.26) | 0.58 (0.47-0.69) | 1052 cm$^{-1}$ (1043-1064) |

Detected biomarker band was not constant and prominent at the appearance in IR spectra measured in the patients with melanocytic nevi (only in 26 spectra out of totally measured 48 spectra in 4 patients), in comparison to SCC (in all spectra measured in 2 patients among 3 patients with MM).

Mean value of a biomarker for melanocytic nevus was 0.20 with a variation between 0.17 and 0.24, similar to mean value of 0.20 for MM, with a variation between 0.14 and 0.26.

The intensity of a biomarker band by the intensity ratio $I_{1055}/I_{1245}$ was similar in the patients with melanocytic nevus and MM.

There was detected a similar left-shifted position of mean peak at 1053 cm$^{-1}$ in the patients with melanocytic nevus and at 1052 cm$^{-1}$ in the patients with MM, with the only difference that mean peak in the patients with melanocytic nevus variated between 1053 cm$^{-1}$ and 1055 cm$^{-1}$, but in the patients with MM mean peak has had large variation between 1043 cm$^{-1}$ and 1064 cm$^{-1}$.

Tumour-Related Detection of the Multiplet (1055 cm$^{-1}$) with DNA/RNA Triad Peak (1071, 1084, 1095 cm$^{-1}$) Patterns In IR absorption spectra from benign, premalignant and malignant skin cancerous tissues the multiplet at about 1055 cm$^{-1}$ is always bounded with DNA/RNA triad peaks at about 1071, 1084 and 1095 cm$^{-1}$ at different shapes and intensities, related to pathology type of skin tumours.

Moreover, the activity of the multiplet has been reported to interact with the activity of the most prominent peak in DNA/RNA triad peak in the patients with different epidermal skin cancers [PCT/EE2013/000001].

Example 1

Basal Cell Carcinoma (BCC)

Table 1 summarizes epidermally detected mean values of a biomarker at about 1055 cm$^{-1}$ and mean values of the peaks in DNA/RNA triad at about 1071, 1084/1085 and 1095 cm$^{-1}$ in 6 patients with BCC.

| BCC | 1055 cm$^{-1}$ | 1071 cm$^{-1}$ | 1084/1085 cm$^{-1}$ | 1095 cm$^{-1}$ |
|---|---|---|---|---|
| 1 pt. | 0.44 | x | 0.45 | x |
| 2 pt. | 0.43 | 0.36 | 0.48 | 0.36 |
| 3 pt. | 0.42 | x | 0.40 | x |
| 4 pt. | 0.19 | x | 0.23 | 0.08 |
| 5 pt. | 0.14 | x | 0.18 | x |
| 6 pt. | 0.09 | x | 0.16 | x |

In all patients with BCC detected biomarker band at about 1055 cm$^{-1}$ is clearly tied with the appearance of DNA/RNA triad peaks at about 1071, 1084/1085 and 1095 cm$^{-1}$.

Results displayed in Table 1 identify 3 patterns:
1055 cm$^{-1}$ with 1084/1085 cm$^{-1}$ (in 4 patients)
1055 cm$^{-1}$ with 1071, 1084/1085, 1095 cm$^{-1}$ (in 1 patient)
1055 cm$^{-1}$ with 1084/1085, 1095 cm$^{-1}$ (in 1 patient)

Example 2

Squamous Cell Carcinoma (SCC)

Table 2 summarizes epidermally detected mean values of a biomarker at about 1055 cm$^{-1}$ and mean values of the peaks in DNA/RNA triad at about 1071, 1084/1085 and 1095 cm$^{-1}$ in 4 patients with SCC.

| SCC | 1055 cm$^{-1}$ | 1071 cm$^{-1}$ | 1084/1085 cm$^{-1}$ | 1095 cm$^{-1}$ |
|---|---|---|---|---|
| 1 pt. | 0.66 | x | 0.65 | x |
| 2 pt. | 0.30 | 0.35 | 0.29 | 0.34 |
| 3 pt. | 0.13 | x | 0.16 | 0.14 |
| 4 pt. | x | 0.11 | 0.12 | 0.09 |

In all patients with SCC detected biomarker band at about 1055 cm$^{-1}$ is clearly tied with the appearance of DNA/RNA triad peaks at about 1071, 1084/1085 and 1095 cm$^{-1}$.

Results displayed in Table 1 identify 3 patterns:
1055 cm$^{-1}$ with 1084/1085 cm$^{-1}$ (in 1 patient)
1055 cm$^{-1}$ with 1071, 1084/1085, 1095 cm$^{-1}$ (in 2 patients)
1055 cm$^{-1}$ with 1084/1085, 1095 cm$^{-1}$ (in 1 patient)

Example 3

Malignant Melanoma (MM)

Table 3 summarizes epidermally detected mean values of a biomarker at about 1055 cm$^{-1}$ and mean values of the peaks in DNA/RNA triad at about 1071, 1084/1085 and 1095 cm$^{-1}$ in 3 patients with MM.

| MM | 1055 cm$^{-1}$ | 1071 cm$^{-1}$ | 1084/1085 cm$^{-1}$ | 1095 cm$^{-1}$ |
|---|---|---|---|---|
| 1 pt. | 0.26 | 0.27 | 0.29 | 0.30 |
| 2 pt. | 0.14 | x | 0.27 | 0.18 |
| 3 pt. | x | x | 0.35 | x |

In all patients with MM detected biomarker band at about 1055 cm$^{-1}$ is clearly tied with the appearance of DNA/RNA triad peaks at about 1071, 1084/1085 and 1095 cm$^{-1}$.

Results displayed in Table 1 identify 3 patterns:
1055 cm$^{-1}$ with 1071, 1084/1085, 1095 cm$^{-1}$ (in 1 patient)
1055 cm$^{-1}$ with 1084/1085, 1095 cm$^{-1}$ (in 1 patient)
no detection of 1055 cm$^{-1}$ with detected 1084/1085 cm$^{-1}$ (in 1 patient)

Example 4

Bowen's Disease

Table 4 summarizes epidermally detected mean values of a biomarker at about 1055 cm$^{-1}$ and mean values of the peaks in DNA/RNA triad at about 1071, 1084/1085 and 1095 cm$^{-1}$ in 3 patients with Bowen's disease.

| Bowen's disease | 1055 cm$^{-1}$ | 1071 cm$^{-1}$ | 1084/1085 cm$^{-1}$ | 1095 cm$^{-1}$ |
|---|---|---|---|---|
| 1 pt. | x | x | 0.07 | x |
| 2 pt. | 0.15 | x | 0.18 | x |
| 3 pt. | 0.26 | x | 0.29 | x |

In all patients with Bowen's disease detected biomarker band at about 1055 cm$^{-1}$ is clearly tied with the appearance of DNA/RNA triad peaks at about 1071, 1084/1085 and 1095 cm$^{-1}$.

Results displayed in Table 1 identify 2 patterns:
1055 cm$^{-1}$ with 1084/1085 cm$^{-1}$ (in 2 patients)
no detection of 1055 cm$^{-1}$ with detected 1084/1085 cm$^{-1}$ (in 1 patient)

Example 5

Melanocytic Nevus

Table 5 summarizes epidermally detected mean values of a biomarker at about 1055 cm$^{-1}$ and mean values of the peaks in DNA/RNA triad at about 1071, 1084/1085 and 1095 cm$^{-1}$ in 4 patients with melanocytic nevi.

| MN | 1055 cm$^{-1}$ | 1071 cm$^{-1}$ | 1084/1085 cm$^{-1}$ | 1095 cm$^{-1}$ |
|---|---|---|---|---|
| 1 pt. | 0.22 | 0.22 | 0.24 | x |
| 2 pt. | 0.19 | 0.20 | 0.23 | x |
| 3 pt. | 0.24 | x | 0.27 | x |
| 4 pt. | 0.17 | 0.16 | 0.19 | x |

In all patients with melanocytic nevi detected biomarker band at about 1055 cm$^{-1}$ is clearly tied with the appearance of DNA/RNA triad peaks at about 1071, 1084/1085 and 1095 cm$^{-1}$.

Results displayed in Table 1 identify 2 patterns:
1055 cm$^{-1}$ with 1084/1085 cm$^{-1}$ (in 1 patient)
1055 cm$^{-1}$ with 1071, 1084/1085 cm$^{-1}$ (in 3 patients)

Example 6

Healthy Epidermis vs. BD vs. MN vs. MM vs. BCC vs. SCC

Table 6 summarizes epidermally detected mean values of a biomarker at about 1055 cm$^{-1}$ and mean values of the peaks in DNA/RNA triad at about 1071, 1084/1085 and 1095 cm$^{-1}$ in 4 healthy subjects, in 3 patients with Bowen's disease, in 4 patients with melanocytic nevi, in 3 patients with MM, in 4 patients with SCC and 6 patients with BCC.

| PATIENTS | 1055 cm$^{-1}$ | 1071 cm$^{-1}$ | 1084/1085 cm$^{-1}$ | 1095 cm$^{-1}$ |
|---|---|---|---|---|
| healthy epidermis | x | 0.50 | 0.30 | 0.50 |
| Bowen's disease | 0.21 | x | 0.18 | x |
| melanocytic nevus | 0.21 | 0.19 | 0.23 | x |
| MM | 0.20 | 0.27 | 0.31 | 0.24 |
| SCC | 0.36 | 0.23 | 0.31 | 0.19 |
| BCC | 0.29 | 0.36 | 0.32 | 0.22 |

Results displayed in Table 6 detect biomarker band at about 1055 cm$^{-1}$ in all measured pathologies in the epidermis (BCC, SCC, MM, Bowen's disease, melanocellular nevus), but with no detection of a biomarker band in healthy, non-pathological epidermis.

Mean values of detected biomarker band at about 1055 cm$^{-1}$ for benign at 0.21, premalignant at 0.21 and malignant skin tumours at 0.20 for MM, at 0.29 for BCC, and at 0.36 for SCC are significant.

However, alone, mean values of a biomarker in 6 patients with BCC and 2 patients with SCC are much more higher than mean values of a biomarker in 2 patients with MM, 4 patients with MN and 3 patients with Bowen's disease.

Importantly, epidermally detected biomarker band in 2 patients with MM is strongly tied with the appearance of all peaks in DNA/RNA triad at about 1071, 1084/1085 and 1095 cm$^{-1}$, that is not observed in the patients with melanocytic nevus (benign compound nevus) and Bowen's disease (precancerous dermatosis). The same pattern of a biomarker band detection together with the appearance of all peaks in DNA/RNA triad is observed in SCC and BCC patients.

So, in epidermally measured patients with melanocytic nevus (benign compound nevus) detection of a biomarker band at about 1055 cm$^{-1}$ is tied with the appearance of 2 peaks in DNA/RNA triad, at about 1071 cm$^{-1}$ and 1084/1085 cm$^{-1}$, but never at about 1095 cm$^{-1}$.

In 2 patients with Bowen's disease, mean value of detected biomarker band at 0.20 is tied with the appearance of one peak in DNA/RNA triad, at about 1084/1085 cm$^{-1}$.

The invention method claimed is:

1. A method of spectral patterned detection of a skin tumour biomarker molecular expression profile and its associated combinations with discriminating markers for diagnosing, predicting and prognosing of benign, premalignant and malignant skin tumours in the skin epidermis of a patient by IR spectroscopy, said method comprising:

(i) measuring the IR spectrum of a whole tumourous skin epidermis in the wavenumber region 900-1300 cm$^{-1}$ to detect the spectral pattern of a skin tumour biomarker molecular expression profile and its associated combinations with discriminating markers by determining the presence, absence and/or levels of the measured biomarker of the multiplet at about 1055 cm$^{-1}$, the DNA/RNA ratio of the intensity of two bands of nucleic acids to molecules DNA and RNA, and the associated peaks at about 1071, 1084/1085 and 1095 cm$^{-1}$ in DNA/RNA triad to molecules DNA and RNA to be characteristic for benign, premalignant and malignant skin tumours in a patient, wherein the presence of a biomarker is diagnostic for benign, premalignant and malignant skin tumours of melanoma and non-melanoma types;

(ii) detecting spectral diagnostic criteria of a skin tumour biomarker molecular expression profile by correlating the measurements of the presence of the measured biomarker at about 1055 cm$^{-1}$ throughout a whole tumourous skin epidermis with a total number of IR spectra with identified biomarker band at about 1055 cm$^{-1}$ to be characteristic for benign, premalignant and malignant skin tumours in said patient, wherein a constant expression is characteristic for malignant skin tumours of melanoma and non-melanoma types, a non-constant expression is characteristic for benign and premalignant skin tumours;

(iii) further detecting spectral diagnostic criteria of a skin tumour biomarker molecular expression profile by correlating the measurements of the presence of the measured biomarker at about 1055 cm$^{-1}$ with the peak position and/or its shifts in IR spectra to be characteristic for benign, premalignant and malignant skin tumours in said patient, wherein a left-shifted mean peak position below 1055 cm$^{-1}$ is characteristic for benign, premalignant and malignant skin tumours of melanoma type, a right-shifted mean peak position above 1055 cm$^{-1}$ is characteristic for malignant skin tumours of non-melanoma type;

(iv) further detecting spectral diagnostic criteria of a skin tumour biomarker molecular expression profile by correlating the measurements of the level of the measured biomarker at about 1055 cm$^{-1}$ with the peak value and/or its intensity in IR spectra to be characteristic for benign, premalignant and malignant skin tumours in said patient, wherein mean values within about 0.20-0.21 with mean intensities within about 0.68-0.72 are characteristic for benign and premalignant skin tumours, mean values within about 0.21 with mean intensities within about 0.58 are characteristic for malignant skin tumours of melanoma type, mean values within about 0.30-0.36 with mean intensities within about 0.83-0.86 are characteristic for malignant skin tumours of non-melanoma type;

(v) determining the spectral pattern of a skin tumour biomarker molecular expression profile in correlation with the measurements of the measured biomarker at about 1055 cm$^{-1}$ in steps (i)-(iv) in said patient with benign, premalignant or malignant skin tumours of melanoma or non-melanoma type in association with a certain tumour type, wherein a biomarker with characteristic predominant non-constant expression in a total number of IR spectra throughout a whole tumourous skin epidermis, predominant left-shifted position of about 1054 cm$^{-1}$ or within mean position variation range of about 1053-1055 cm$^{-1}$, mean peak values of about 0.20 or within mean numerical variation range of about 0.17-0.24, mean peak intensities of about 0.68 or within mean numerical variation range of about 0.59-0.75, to be diagnostic for benign skin tumours in association with melanocytic nevus (MN), or a biomarker with characteristic dominant non-constant expression in a total number of IR spectra throughout a whole tumourous skin epidermis, left-shifted mean peak position of about 1053 cm$^{-1}$ or within mean position variation range of about 1052-1053 cm$^{-1}$, mean peak values of about 0.21 or within mean numerical variation range of about 0.15-0.26, mean peak intensities of about 0.72 or within mean numerical variation range of about 0.66-0.77, to be diagnostic for premalignant skin tumours in association with Bowen's disease (BD), or a biomarker with characteristic constant expression in a total number of IR spectra throughout a whole tumourous skin epidermis, predominant most left-shifted mean peak position of about 1052 cm$^{-1}$ or within mean position variation range of about 1050-1054 cm$^{-1}$, mean peak values of about 0.20 or within mean numerical variation range of about 0.14-0.26, mean peak intensities of about 0.58 or within mean numerical variation range of about 0.47-0.69, to be diagnostic for malignant skin tumours in association with malignant melanoma (MM), or a biomarker with characteristic constant expression in a total number of IR spectra throughout a whole tumourous skin epidermis, prevailing right-shifted mean peak position of about 1057 cm$^{-1}$ or within mean position variation range of about 1054-1060 cm$^{-1}$, mean peak values of about 0.36 or within mean numerical variation range of about 0.13-0.66, mean peak intensities of about 0.86 or within mean numerical variation range of about 0.77-1.00, to be diagnostic for malignant skin tumours in association with squamous cell carcinoma (SCC), or a biomarker with characteristic constant expression in a total number of IR spectra throughout a whole tumourous skin epidermis, predominant most right-shifted mean peak position of about 1058 cm$^{-1}$ or within mean peak position variation range of about 1053-1062 cm$^{-1}$, mean peak values of about 0.30 or within mean numerical variation range of about 0.09-0.44, mean peak intensities of about 0.83 or within mean numerical variation range of about 0.59-0.96, to be diagnostic for malignant skin tumours in association with basal cell carcinoma (BCC);

(vi) detecting spectral pattern of a skin tumour biomarker molecular expression profile and its associated combinations with discriminating markers by further correlating said measurements of the presence, absence and/or level of the measured biomarker at about 1055 cm$^{-1}$ with the presence, absence and/or level of the measured peak(s) at about 1071, 1084/1085 and/or 1095 cm$^{-1}$ in DNA/RNA triad against the absence of the measured biomarker together with the presence of the peaks at the level of about 0.50 at about 1071 cm$^{-1}$, at the level of about 0.30 at about 1084/1085 cm$^{-1}$ and at the level of about 0.50 at about 1095 cm$^{-1}$ in DNA/RNA triad in healthy skin epidermis, to be further associated with benign, premalignant or malignant skin tumours of melanoma or non-melanoma type in association with a certain tumour type, wherein a combination of a biomarker and discriminating markers with characteristic spectral parameters at about 1055 cm$^{-1}$, 1071 cm$^{-1}$ and 1084/1085 cm$^{-1}$, with characteristic mean peak values at about 1055 cm$^{-1}$ of about 0.20 or within mean numerical variation range of about 0.17-0.24, at about 1071 cm$^{-1}$ of about 0.19 or within mean numerical variation range of 0.16-0.22, at about 1084/1085 cm$^{-1}$ of about 0.23 or within mean numerical variation range of 0.19-0.27, corresponding to one of the patterned appearances in IR spectra at about 1055 cm$^{-1}$ and 1084/1085 cm, or predominantly at about 1055 cm$^{-1}$, 1071 cm$^{-1}$ and 1084/1085 cm$^{-1}$, to be diagnostic for benign skin tumours in association with MN, or a combination of a biomarker and a discriminating marker with characteristic spectral parameters at about 1055 cm$^{-1}$ and 1084/1085 cm$^{-1}$ with characteristic mean peak values at about 1055 cm$^{-1}$ of about 0.21 or within mean numerical variation range of about 0.15-0.26, at about 1084/1085 cm$^{-1}$1 within mean numerical variation range of about 0.18-0.29, corresponding to the patterned appearance in IR spectra predominantly at about 1055 cm$^{-1}$ and 1084/1085 cm$^{-1}$, or the absence of a biomarker with the peak at about 1084/1085 cm$^{-1}$ to be diagnostic for premalignant skin tumours in association with BD, or a combination of a biomarker and discriminating markers with characteristic spectral parameters at about 1055 cm$^{-1}$, 1071 cm$^{-1}$, 1084/1085 cm$^{-1}$ and 1095 cm$^{-1}$ with characteristic mean peak values at about 1055 cm$^{-1}$ of about 0.20 or within mean numerical variation range of about 0.14-0.26, at about 1071 cm$^{-1}$ of about 0.27, at about 1084/1085 cm$^{-1}$ of about 0.31 or within mean numerical variation range of about 0.27-0.35, at about 1095 cm$^{-1}$ of about 0.24 or within mean numerical variation range of about 0.18-0.30, corresponding to one of the patterned appearances in IR spectra at about 1055 cm$^{-1}$, 1071 cm$^{-1}$, 1084/1085 cm$^{-1}$ and 1095 cm$^{-1}$, or at about 1055 cm$^{-1}$, 1084/1085 cm$^{-1}$ and 1095 cm$^{-1}$, or the absence of a biomarker with the peak at about 1084/1085 cm, to be diagnostic for malignant skin tumours of melanoma type in association with MM, or a combination of a biomarker and discriminating markers with characteristic spectral parameters at about 1055 cm$^{-1}$, 1071 cm$^{-1}$1, 1084/1085 cm$^{-1}$ and 1095 cm$^{-1}$ with characteristic mean peak values at about 1055 cm$^{-1}$ of about 0.36 or within mean numerical variation range of about 0.13-0.66, at about 1071 cm$^{-1}$ of about 0.23 or within mean numerical variation range of about 0.11-0.35, at about 1084/1085 cm$^{-1}$ of about 0.31 or within mean numerical variation range of about 0.12-0.65, at about 1095 cm$^{-1}$1 of about 0.19 or within mean numerical variation range of about 0.09-0.34, corresponding to one of the patterned appearances in IR spectra at about 1055 cm$^{-1}$, 1071 cm$^{-1}$, 1084/1085 cm$^{-1}$ and 1095 cm$^{-1}$, or at about 1055 cm$^{-1}$, 108411085 cm$^{-1}$ and 1095 cm$^{-1}$, or at about 1055 cm$^{-1}$ and 1084/1085 cm$^{-1}$, or the absence of a biomarker with the peaks at about 1055 cm$^{-1}$, 1071 cm$^{-1}$, 108411085 cm$^{-1}$ and 1095 cm$^{-1}$, to be diagnostic for malignant skin tumours of non-melanoma type in association with SCC, or a combination of a biomarker and discriminating markers with characteristic spectral parameters at about 1055 cm$^{-1}$, 1071 cm$^{-1}$1, 1084/1085 cm$^{-1}$ and 1095 cm$^{-1}$ with characteristic mean peak values at about 1055 cm$^{-1}$ of about 0.30 or within mean numerical variation range of about 0.09-0.44, at about 1071 cm$^{-1}$ of about 0.36, at about 1084/1085 cm$^{-1}$ of about 0.32 or within mean numerical variation range of about 0.16-0.45, at about 1095 cm$^{-1}$ of about 0.22 or within mean numerical variation range of about 0.08-0.36, corresponding to one of the patterned appearances in IR spectra at about 1055 cm$^{-1}$, 1071 cm$^{-1}$, 1084/1085 cm$^{-1}$ and 1095 cm$^{-1}$, or at about 1055 cm$^{-1}$, 1084/1085 cm$^{-1}$ and 1095 cm$^{-1}$, or predominantly at about 1055 cm$^{-1}$ and 1084/1085 cm$^{-1}$, to be diagnostic for malignant skin tumours of non-melanoma type in association with BCC; and (vii) diagnosing said patient with benign skin tumours in association with MN, or premalignant skin tumours in association with BD, or malignant skin tumours of melanoma type in association with MM, or malignant skin tumours of non-melanoma type in association with SCC, or malignant skin tumours of non-melanoma type in association with BCC, when corresponding spectral pattern of a skin tumour biomarker molecular expression profile according to step (v) and its associated combination of molecular expression of discriminating markers according to step (vi) in correlation with characteristic measurements of the presence, absence and/or levels of the measured biomarker at about 1055 cm$^{-1}$ and/or the peak(s) at about 1071, 1084/1085 and/or 1095 cm$^{-1}$ in DNA/RNA triad is detected, wherein diagnosing the patient with MN when one among 2 MN spectral patterns of said non-constant presence of a biomarker at prevailing left-shifted peak position along with said presence of the peaks at about 1071 cm$^{-1}$ and 1084/1085 cm$^{-1}$ within said mean values and/or intensity ranges, or said non-constant presence of a biomarker at prevailing left-shifted peak position along with said presence of the peak at about 1084/1085 cm$^{-1}$ within said mean values and/or intensity ranges throughout a whole tumourous skin epidermis of a patient is detected, or diagnosing the patient with BD when one among 2 BD spectral patterns of said non-constant presence of a biomarker at prevailing left-shifted peak position along with 1 peak at about 1084/1085 cm$^{-1}$ within said mean values and/or intensity ranges, or said absence of a biomarker along with 1 peak at about 1084/1085 cm$^{-1}$ within said mean values and/or intensity ranges throughout a whole tumourous skin epidermis of a patient is detected, or diagnosing the patient with MM when one among 3 MM spectral patterns of said constant presence of a biomarker at the most left-shifted peak position along with 3 peaks at about 1071, 1084/1085 and 1095 cm$^{-1}$ within said mean values and/or intensity ranges, or said constant presence of a biomarker at the most left-shifted peak position along with 2 peaks at about 1084/1085 and 1095 cm$^{-1}$ within said mean values and/or intensity ranges, or said absence of a biomarker along with 1 peak at about 1084/1085 cm$^{-1}$ within said mean values and/or intensity ranges throughout a whole tumourous skin epidermis of a patient is detected, or diagnosing the patient with SCC when one among 4 said SCC spectral patterns of said constant presence of a biomarker at the right-shifted peak position along with 3 peaks at about 1071, 1084/1085 and 1095 cm$^{-1}$ within said mean values and/or intensity ranges, or said constant presence of a biomarker at the right-shifted peak position along with 2 peaks at about 1084/1085 and 1095 cm$^{-1}$ within said mean values and/or intensity ranges, or said constant presence of a biomarker at the right-shifted peak position along with 1 peak at about 1084/1085 cm$^{-1}$ within said mean values and/or intensity ranges, or said absence of a biomarker along with 3 peaks about 1071, 1084/1085 and 1095 cm$^{-1}$ within said mean values and/or intensity ranges throughout a whole tumourous skin epidermis of a patient is detected, or diagnosing the patient with BCC, when one among 3 said BCC spectral patterns of said constant presence of a biomarker at the most right-shifted peak position along with 3 peaks at about 1071, 1084/1085 and 1095 cm$^{-1}$ within said mean values and/or intensity ranges, or said constant presence of a biomarker at the most right-shifted peak position along with 2 peaks at about 1084/1085 and 1095 cm$^{-1}$ within said mean values and/or intensity ranges, or said constant presence of a biomarker at the most right-shifted peak position along with 1 peak at about 1084/1085 cm$^{-1}$ within said mean values and/or intensity ranges throughout a whole tumourous skin epidermis of a patient is detected.

2. A method of stratifying a patient with a skin cancer of melanoma or non-melanoma type or at the risk of developing a skin cancer of melanoma or non-melanoma type by monitoring a progression towards malignancy in said patient with benign skin tumours in association with a certain tumour type or with premalignant tumours in association with a certain tumour type, or by monitoring a progression of malignancy in said patient with malignant skin tumours of melanoma or non-melanoma type, the method comprising the steps (i-vii) according to claim 1, and (viii) monitoring the change of the spectral pattern of a skin tumour biomarker molecular expression profile and its associated combinations with discriminating markers for stratifying the patient identified in step (vii) as having, or being at the risk of developing, a skin cancer of melanoma or non-melanoma type, to a screening and follow-up regimen for preventing a skin cancer progression in said patient with a certain skin cancer melanoma or non-melanoma type or for preventing a progression towards a skin cancer of melanoma and non-melanoma type in said patient with benign skin tumours in association with a certain tumour type or with premalignant skin tumours in association with a certain tumour type.

3. A method of stratifying a patient to a therapeutic regimen for treating or preventing a skin cancer of melanoma or non-melanoma type by determining prognosis of the treatment in said patient or predicting the treatment in said patient with benign, premalignant or malignant skin tumours in association with a certain type, the method comprising the steps (i-vii) according to claim 1, and (viii) monitoring the change of the spectral pattern of a skin tumour biomarker molecular expression profile and its associated combinations with discriminating markers for stratifying the patient identified in step (vii), as having, or being at the risk of developing a skin cancer of melanoma or non-melanoma type, to a therapeutic regimen for treating or preventing a skin cancer of melanoma or non-melanoma type in said patient.

4. A method of monitoring the spectral pattern of a skin tumour biomarker molecular profile at about 1055 cm$^{-1}$ and its combinations associated with molecular expression of discriminating markers at about 1071, 1084/1085 and/or 1095 cm$^{-1}$ in the skin epidermis of a patient for differential diagnosis between benign, premalignant and malignant skin tumours of melanoma and non-melanoma types in a patient, or in a method for monitoring a progression towards malignancy in a patient with benign or premalignant skin tumours in association with a certain type, or for monitoring a progression of malignancy in a patient with malignant skin tumours of melanoma or non-melanoma type, or for determination of the most effective therapy in a patient with benign, premalignant or malignant skin tumours in association with a certain skin tumour type, or for determination of the most effective dosage of drug in a patient with benign, premalignant or malignant skin tumours in association with a certain skin tumour type, the method comprising the steps according to claim.

5. The method according to claim 1, further comprising: screening and follow-up of benign skin tumours for skin cancer prevention in a patient with MN, wherein the change of the spectral pattern of a skin tumour biomarker molecular expression profile and its associated combinations with discriminating markers to one of the spectral patterns of a skin tumour biomarker molecular expression profile and its associated combinations with discriminating markers to be diagnostic for malignant skin tumours of melanoma type in said patient with previously detected benign skin tumour in association with MN, indicates malignant skin tumour of melanoma type in association with MM in the same patient.

6. The method according to claim 1, further comprising: screening and follow-up of premalignant skin tumours for skin cancer prevention in a patient with BD, wherein the change of the spectral pattern of a skin tumour biomarker molecular expression profile and its associated combinations with discriminating markers to one of the spectral patterns of a skin tumour biomarker molecular expression profile and its associated combinations with discriminating markers to be diagnostic for malignant skin tumour of non-melanoma type in said patient with previously detected premalignant skin tumour in association with BD, indicates malignant skin tumour of non-melanoma type in association with SCC in the same patient.

7. The method according to claim 1, further comprising: screening or follow-up of malignant skin tumours for skin cancer progression/regression in a patient with MM, SCC or BCC, wherein the change of the spectral pattern of a skin tumour biomarker molecular expression profile and its associated combinations with discriminating markers to one of the spectral patterns of a skin tumour biomarker molecular expression profile and its associated combinations with discriminating markers to be diagnostic for malignant skin tumours in a patient with previously detected malignant skin tumour in association with MM, SCC or BCC, indicates a cancer progression in said patient with malignant skin tumour in association with a certain skin cancer type.

8. The method of claim 1, wherein said benign, premalignant and malignant tumours of skin tissue are selected from the group of benign melanocytic nevus, Bowen's disease, basal cell carcinoma, squamous cell carcinoma, malignant melanoma, also comprise other benign, premalignant and malignant tumours of melanoma and non-melanoma of skin tissue.

9. The method of claim 1, further comprising:
(viii) further detecting and analysing the spectral pattern of a skin tumour biomarker molecular expression profile and/or by the spectral pattern monitoring of a skin tumour biomarker molecular expression profile in the irradiated skin epidermis of a patient for aiding the field of personalized medicine for the therapeutic and/or prophylactic treatment of benign, premalignant and malignant skin tumours in a patient, or for determination of prognosis of the treatment of benign, premalignant and malignant skin tumours in a patient, or for prediction of the treatment of benign, premalignant and malignant skin tumour in a patient.

10. The method of claim 1, further comprising:
(viii) further detecting and analysing the spectral pattern of a skin tumour biomarker molecular expression profile and/or by the spectral pattern monitoring of a skin tumour biomarker molecular expression profile in the irradiated skin epidermis of a patient on FTIR spectrometer for easy visualization of cellular components based on their intrinsic properties and chemical composition without a requirement of external contrast-inducing agents for diagnosis, prognosis and prediction of benign, premalignant and malignant skin tumours in association with a certain type of skin tumour and/or malignancy in a patient.

11. The method of claim 1, further comprising:
(viii) further detecting spectral diagnostic criteria of associated discriminating markers with characteristic spectral parameters at consistent and significant absorption wave numbers at about 1071 cm$^{-1}$, 1084l1085 cm$^{-1}$ and 1095 cm$^{-1}$ in DNA/RNA triad corresponding to identity and secondary structures to molecules DNA and RNA in correlation with characteristic measurements of the presence, absence and levels of the measured biomarker at about 1055 cm and the peak(s) at about 1071, 1084/1085 and/or 1095 cm$^{-1}$ in DNA/RNA triad on FTIR spectrometer in the irradiated skin epidermis of a patient, when used for detecting, predicting and prognosing benign, premalignant and malignant skin tumours in a patient, and/or when used for screening and follow-up of benign, premalignant and malignant skin tumours in a patient, which is one selected from:
(i) a combination group of nucleic acids molecules with characteristic spectral parameters at about 1055 cm$^{-1}$, 1071 cm$^{-1}$ and 1084/1085 cm$^{-1}$ with characteristic mean peak values at about 1055 cm$^{-1}$ of about 0.20 or within mean numerical variation range of about 0.17-0.24, at about 1071 cm$^{-1}$ of about 0.19 or within mean numerical variation range of 0.16-0.22, at about 1084/1085 cm$^{-1}$ of about 0.23 or within mean numerical variation range of 0.19-0.27 on FTIR spectrometer,
corresponding to one of the patterned appearances of nucleic acids molecules in IR spectra
at about 1055 cm$^{-1}$, 1071 cm$^{-1}$ and 1084/1085 cm, or
at about 1055 cm$^{-1}$ and 1084/1085 cm$^{-1}$,
to be diagnostic for benign skin tumours in association with MN; or
(ii) a combination group of nucleic acids molecules with characteristic spectral parameters at about 1055 cm$^{-1}$ and 1084/1085 cm$^{-1}$ with characteristic mean peak values at about 1055 cm$^{-1}$ of about 0.21 or within mean numerical variation range of about 0.15-0.26, at about 1084/1085 cm$^{-1}$ within mean numerical variation range of about 0.18-0.29 on FTIR spectrometer,
corresponding to the patterned appearance of nucleic acids molecules in IR spectra
at about 1055 cm$^{-1}$ and 1084/1085 cm$^{-1}$,
to be diagnostic for premalignant skin tumours in association with BD; or
(iii) a combination group of nucleic acids molecules with characteristic spectral parameters at about 1055 cm$^{-1}$, 1071 cm$^{-1}$, 1084/1085 cm$^{-1}$ and 1095 cm$^{-1}$ with characteristic mean peak values at about 1055 cm$^{-1}$ of about 0.20 or within mean numerical variation range of about 0.14-0.26, at about 1071 cm$^{-1}$ of about 0.27, at about 1084/1085 cm$^{-1}$ of about 0.31 or within mean numerical variation range of about 0.27-0.35, at about 1095 cm$^{-1}$ of about 0.24 or within mean numerical variation range of about 0.18-0.30 on FTIR spectrometer,
corresponding to one of the patterned appearances of nucleic acids molecules in IR spectra
at about 1055 cm$^{-1}$, 1071 cm$^{-1}$, 1084/1085 cm$^{-1}$ and 1095 cm$^{-1}$, or
at about 1055 cm$^{-1}$, 1084/1085 cm$^{-1}$ and 1095 cm$^{-1}$,
to be diagnostic for malignant skin tumours of melanoma type in association with MM: or
(iv) a combination group of nucleic acids molecules with characteristic spectral parameters at about 1055 cm$^{-1}$, 1071 cm$^{-1}$, 1084/1085 cm$^{-1}$ and 1095 cm$^{-1}$ with characteristic mean peak values at about 1055 cm$^{-1}$ of about 0.36 or within mean numerical variation range of about 0.13-0.66, at about 1071 cm$^{-1}$ of about 0.23 or within mean numerical variation range of about 0.11-0.35, at about 1084/1085 cm$^{-1}$ of about 0.31 or within mean numerical variation range of about 0.12-0.65, at about 1095 cm$^{-1}$ of about 0.19 or within mean numerical variation range of about 0.09-0.34 on FTIR spectrometer, corresponding to one of the patterned appearances of nucleic acids molecules in IR spectra
at about 1055 cm$^{-1}$, 1071 cm$^{-1}$, 1084/1085 cm$^{-1}$ and 1095 cm$^{-1}$, or
at about 1055 cm$^{-1}$, 1084/1085 cm$^{-1}$ and 1095 cm$^{-1}$, or
at about 1055 cm$^{-1}$ and 1084/1085 cm$^{-1}$,
to be diagnostic for malignant skin tumours of non-melanoma type in association with SCC; or
(v) a combination group of nucleic acids molecules with characteristic spectral parameters at about 1055 cm-1, 1071 cm-1, 104/1085 cm-1 and 1095 cm-1 with characteristic mean peak values at about 1055 cm-1 of about 0.30 or within mean numerical variation range of about 0.09-0.44, at about 1071 cm-1 of about 0.36, at about 1084/1085 cm-1 of about 0.32 or within mean numerical variation range of about 0.16-0.45, at about 1095 cm-1 of about 0.22 or within mean numerical variation range of about 0.08-0.36 on FTIR spectrometer,
corresponding to one of the patterned appearances of nucleic acids molecules in IR spectra
at about 1055 cm$^{-1}$, 1071 cm, 1084/1085 cm$^{-1}$ and 1095 cm$^{-1}$,
at about 1055 cm$^{-1}$, 1084/1085 cm$^{-1}$ and 1095 cm$^{-1}$, or
at about 1055 cm$^{-1}$ and 1084/1085 cm$^{-1}$,
to be diagnostic for malignant skin tumours of non-melanoma type in association with BCC,
(ix) diagnosing said patient with benign skin tumours in association with MN, or premalignant skin tumours in association with BD, or malignant skin tumours of melanoma type in association with MM, or malignant skin tumours of non-melanoma type in association with SCC, or malignant skin tumours of non-melanoma type in association with BCC, when corresponding spectral pattern of a skin tumour biomarker molecular expression profile according to step (v) and its associated combination of molecular expression of discriminating markers according to step (vi) in correlation with characteristic measurements of the presence, absence and/or levels of the measured biomarker at about 1055 cm$^{-1}$ and/or the peak(s) at about 1071, 1084/1085 and/or 1095 cm$^{-1}$ in DNA/RNA triad is detected, wherein diagnosing the patient with MN when one among 2 MN spectral patterns of said non-constant presence of a biomarker at prevailing left-shifted peak position along with said presence of the peaks at about 1071 cm$^{-1}$ and 1084/1085 cm$^{-1}$ within said mean values and/or intensity ranges, or said non-constant presence of a biomarker at prevailing left-shifted peak position along with said presence of the peak at about 1084/1085 cm$^{-1}$ within said mean values and/or intensity ranges throughout a whole tumourous skin epidermis of a patient is detected, or diagnosing the patient with BD when one among 2 BD spectral patterns of said non-constant presence of a biomarker at prevailing left-shifted peak position along with 1 peak at about 1084/1085 cm$^{-1}$ within said mean values and/or intensity ranges, or said absence of a biomarker along with 1 peak at about 1084/1085 cm$^{-1}$ within said mean values and/or intensity ranges throughout a whole tumourous skin epidermis of a patient is detected, or diagnosing the patient with MM when one among 3 MM spectral patterns of said constant presence of a biomarker at the most left-shifted peak position along with 3 peaks at about 1071, 1084/1085 and 1095 cm$^{-1}$ within said mean values and/or intensity ranges, or said constant presence of a biomarker at the most left-shifted peak position along with 2 peaks at about 10841085 and 1095 cm$^{-1}$ within said mean values and/or intensity ranges, or said absence of a biomarker along with 1 peak at about 1084/1085 cm$^{-1}$ within said mean values and/or intensity ranges throughout a whole tumourous skin epidermis of a patient is detected, or diagnosing the patient with SCC when one among 4 said SCC spectral patterns of said constant presence of a biomarker at the right-shifted peak position along with 3 peaks at about 1071, 1084/1085 and 1095 cm$^{-1}$ within said mean values and/or intensity ranges, or said constant presence of a biomarker at the right-shifted peak position along with 2 peaks at about 1084/1085 and 1095 cur within said mean values and/or intensity ranges, or said constant presence of a biomarker at the right-shifted peak position along with 1 peak at about 1084/1085 cm$^{-1}$ within said mean values and/or intensity ranges, or said absence of a biomarker along with 3 peaks about 1071, 1084/1085 and 1095 cm$^{-1}$ within said mean values and/or intensity ranges throughout a whole tumourous skin epidermis of a patient is detected, or diagnosing the patient with BCC, when one among 3 said BCC spectral patterns of said constant presence of a biomarker at the most right-shifted peak position along with 3 peaks at about 1071, 1084/1085 and 1095 cm$^{-1}$ within said mean values and/or intensity ranges, or said constant presence of a biomarker at the most right-shifted peak position along with 2 peaks at about 1084/1085 and 1095 cm$^{-1}$ within said mean values and/or intensity ranges, or said constant presence of a biomarker at the most right-shifted peak position along with 1 peak at about 1084/1085 cm$^{-1}$ within said mean values and/or intensity ranges throughout a whole tumourous skin epidermis of a patient is detected.

12. The method of claim 11 further comprising the steps:
(x) detecting and analyzing the spectral expression pattern of a skin tumour biomarker and its associated discriminating markers and/or by the spectral expression pattern monitoring of a skin tumour biomarker molecular expression profile in the irradiated skin epidermis of a patient on FTIR spectrometer for aiding the field of personalized medicine for the therapeutic and/or prophylactic treatment of benign, premalignant and malignant skin tumours in a patient, or for determination of prognosis of the treatment of benign, premalignant and malignant skin tumours in a patient, or for prediction of the treatment of benign, premalignant and malignant skin tumour in a patient.

13. The method of claim 11 further comprising the steps:
(x) detecting and analysing the spectral expression pattern of a skin tumour biomarker and its associated discriminating markers and/or by the spectral expression pattern monitoring of a skin tumour biomarker molecular expression profile in the irradiated skin epidermis of a patient on FTIR spectrometer for easy visualization of cellular components based on their intrinsic properties and chemical composition without a requirement of external contrast-inducing agents for diagnosis, prognosis and prediction of benign, premalignant and malignant skin tumours of melanoma or non-melanoma type in association with a certain type of skin tumour and/or malignancy in a patient.

14. A method of spectral patterned detection of a tumour biomarker molecular expression profile and its associated combinations with discriminating markers for diagnosing, predicting and prognosing of benign, premalignant and malignant tumours in the tissue of a patient by IR spectroscopy, said method comprising:
(i) measuring the IR spectrum of a whole tumourous tissue in the wavenumber region 900-1300 cm$^{-1}$ to detect the spectral pattern of a tumour biomarker molecular expression profile and its associated combinations with discriminating markers by determining the presence, absence and/or levels of the measured biomarker of the multiplet at about 1055 cm$^{-1}$, the DNA/RNA ratio of the intensity of two bands of nucleic acids to molecules DNA and RNA, and the associated peaks at about 1071, 1084/1085 and 1095 cm$^{-1}$ in DNA/RNA triad to molecules DNA and RNA to be characteristic for benign, premalignant and malignant tumours in a patient, wherein the presence of a biomarker is diagnostic for benign, premalignant and malignant tumours;
(ii) detecting spectral diagnostic criteria of a tumour biomarker molecular expression profile by correlating the measurements of the presence of the measured biomarker at about 1055 cm$^{-1}$ throughout a whole tumourous tissue with a total number of IR spectra with identified biomarker band at about 1055 cm$^{-1}$ to be characteristic for benign, premalignant and malignant tumours in said patient, wherein a constant expression is characteristic for malignant tumours, a non-constant expression is characteristic for benign and premalignant tumours;

(iii) further detecting spectral diagnostic criteria of a tumour biomarker molecular expression profile by correlating the measurements of the presence of the measured biomarker at about 1055 cm$^{-1}$ with the peak position and/or its shifts in IR spectra to be characteristic for benign, premalignant and malignant tumours in said patient, wherein a left-shifted mean peak position below 1055 cm$^{-1}$ is characteristic for benign, premalignant and malignant tumours, a right-shifted mean peak position above 1055 cm$^{-1}$ is characteristic for malignant tumours of non-melanoma type;

(iv) further detecting spectral diagnostic criteria of a tumour biomarker molecular expression profile by correlating the measurements of the level of the measured biomarker at about 1055 cm$^{-1}$ with the peak value and/or its intensity in IR spectra to be characteristic for benign, premalignant and malignant tumours in said patient, wherein mean values within about 0.20-0.21 with mean intensities within about 0.68-0.72 are characteristic for benign and premalignant tumours, mean values within about 0.21 with mean intensities within about 0.58 are characteristic for malignant tumours of melanoma type, mean values within about 0.30-0.36 with mean intensities within about 0.83-0.86 are characteristic for malignant tumours of non-melanoma type;

(v) determining the spectral pattern of a tumour biomarker molecular expression profile in correlation with the measurements of the measured biomarker at about 1055 cm$^{-1}$ in steps (i)-(iv) in said patient with benign, premalignant or malignant tumours of melanoma or non-melanoma type in association with a certain tumour type, wherein a biomarker with characteristic predominant non-constant expression in a total number of IR spectra throughout a whole tumourous tissue, predominant left-shifted position of about 1054 cm$^{-1}$ or within mean position variation range of about 1053-1055 cm$^{-1}$, mean peak values of about 0.20 or within mean numerical variation range of about 0.17-0.24, mean peak intensities of about 0.68 or within mean numerical variation range of about 0.59-0.75, to be diagnostic for benign tumours in association with the certain tumour type from other organs than skin with reference to melanocytic nevus (MN), or a biomarker with characteristic dominant non-constant expression in a total number of IR spectra throughout a whole tumourous tissue, left-shifted mean peak position of about 1053 cm$^{-1}$ or within mean position variation range of about 1052-1053 cm$^{-1}$, mean peak values of about 0.21 or within mean numerical variation range of about 0.15-0.26, mean peak intensities of about 0.72 or within mean numerical variation range of about 0.66-0.77, to be diagnostic for premalignant tumours in association with the certain tumour type from other organs than skin with reference to Bowen's disease (BD), or a biomarker with characteristic constant expression in a total number of IR spectra throughout a whole tumourous tissue, predominant most left-shifted mean peak position of about 1052 cm$^{-1}$ or within mean position variation range of about 1050-1054 cm$^{-1}$, mean peak values of about 0.20 or within mean numerical variation range of about 0.14-0.26, mean peak intensities of about 0.58 or within mean numerical variation range of about 0.47-0.69, to be diagnostic for malignant tumours in association with the certain tumour type from other organs than skin with reference to malignant melanoma (MM), or a biomarker with characteristic constant expression in a total number of IR spectra throughout a whole tumourous tissue, prevailing right-shifted mean peak position of about 1057 cm$^{-1}$ or within mean position variation range of about 1054-1060 cm$^{-1}$, mean peak values of about 0.36 or within mean numerical variation range of about 0.13-0.66, mean peak intensities of about 0.86 or within mean numerical variation range of about 0.77-1.00, to be diagnostic for malignant tumours in association with the certain tumour type from other organs than skin with reference to squamous cell carcinoma (SCC), or a biomarker with characteristic constant expression in a total number of IR spectra throughout a whole tumourous tissue, predominant most right-shifted mean peak position of about 1058 cm$^{-1}$ or within mean peak position variation range of about 1053-1062 cm$^{-1}$, mean peak values of about 0.30 or within mean numerical variation range of about 0.09-0.44, mean peak intensities of about 0.83 or within mean numerical variation range of about 0.59-0.96, to be diagnostic for malignant tumours in association with the certain tumour type from other organs than skin with reference to basal cell carcinoma (BCC);

(vi) detecting spectral pattern of a tumour biomarker molecular expression profile and its associated combinations with discriminating markers by further conelating said measurements of the presence, absence and/or level of the measured biomarker at about 1055 cm$^{-1}$ with the presence, absence and/or level of the measured peak(s) at about 1071, 1084/1085 and/or 1095 cm$^{-1}$ in DNA/RNA triad against the absence of the measured biomarker together with the presence of the peaks at the level of about 0.50 at about 1071 cm$^{-1}$, at the level of about 0.30 at about 1084/1085 cm$^{-1}$ and at the level of about 0.50 at about 1095 cm$^{-1}$ in DNA/RNA triad in healthy tissue, to be further associated with benign, premalignant or malignant tumours of melanoma or non-melanoma type in association with a certain tumour type, wherein a combination of a biomarker and discriminating markers with characteristic spectral parameters at about 1055 cm$^{-1}$, 1071 cm$^{-1}$ and 1084/1085 cm$^{-1}$, with characteristic mean peak values at about 1055 cm$^{-1}$ of about 0.20 or within mean numerical variation range of about 0.17-0.24, at about 1071 cm$^{-1}$ of about 0.19 or within mean numerical variation range of 0.16-0.22, at about 1084/1085 cm$^{-1}$ of about 0.23 or within mean numerical variation range of 0.19-0.27, corresponding to one of the patterned appearances in IR spectra at about 1055 cm$^{-1}$ and 10841085 cm$^{-1}$, or predominantly at about 1055 cm$^{-1}$, 1071 cm$^{-1}$ and 1084/1085 cm$^{-1}$, to be diagnostic for benign tumours in association with the certain tumour type from other organs than skin with reference to MN, or a combination of a biomarker and a discriminating marker with characteristic spectral parameters at about 1055 cm$^{-1}$ and 1084/1085 cm$^{-1}$ with characteristic mean peak values at about 1055 cm$^{-1}$ of about 0.21 or within mean numerical variation range of about 0.15-0.26, at about 1084/1085 cm$^{-1}$ within mean numerical variation range of about 0.18-0.29, corresponding to the patterned appearance in IR spectra predominantly at about 1055 cm$^{-1}$ and 1084/1085 cm$^{-1}$, or the absence of a biomarker with the peak at about 1084/1085 cm$^{-1}$, to be diagnostic for premalignant tumours in association with the certain tumour type from other organs than skin with reference to BD, or a combination of a biomarker and discriminating markers with characteristic spectral parameters at about 1055 cm$^{-1}$, 1071 cm$^{-1}$, 1084/1085 cm$^{-1}$ and 1095 cm$^{-1}$ with characteristic mean peak values at about 1055 cm$^{-1}$ of about 0.20 or within mean numerical variation range of about 0.14-0.26, at about 1071 cm$^{-1}$ of about 0.27, at about 1084/1085 cm$^{-1}$ of about 0.31 or within mean numerical variation range of about 0.27-0.35, at about 1095 cm$^{-1}$ of about 0.24 or within mean numerical variation range of about 0.18-0.30, corresponding to one of the patterned appearances in IR spectra at about 1055 cm$^{-1}$, 1071 cm$^{-1}$, 1084/1085 cm$^{-1}$ and 1095 cm$^{-1}$, or at about 1055 cm$^{-1}$, 1084/1085 cm$^{-1}$ and 1095 cm$^{-1}$, or the absence of a biomarker with the peak at about 1084/1085 cm$^{-1}$, to be diagnostic for malignant tumours of melanoma type in association with the certain tumour type from other organs than skin with reference to MM, or a combination of a biomarker and discriminating markers with characteristic spectral parameters at about 1055 cm$^{-1}$, 1071 cm$^{-1}$, 1084/1085 cm$^{-1}$ and 1095 cm$^{-1}$ with characteristic mean peak values at about 1055 cm$^{-1}$ of about 0.36 or within mean numerical variation range of about 0.13-0.66, at about 1071 cm$^{-1}$ of about 0.23 or within mean numerical variation range of about 0.11-0.35, at about 1084/1085 cm$^{-1}$ of about 0.31 or within mean numerical variation range of about 0.12-0.65, at about 1095 cm$^{-1}$ of about 0.19 or within mean numerical variation range of about 0.09-0.34, corresponding to one of the patterned appearances in IR spectra at about 1055 cm$^{-1}$1, 1071 cm$^{-1}$, 1084/1085 cm$^{-1}$ and 1095 cm$^{-1}$, or at about 1055 cm$^{-1}$, 1084/1085 cm$^{-1}$ and 1095 cm-r, or at about 1055 cm$^{-1}$ and 1084/1085 cm$^{-1}$, or the absence of a biomarker with the peaks at about 1055 cm$^{-1}$, 1071 cm$^{-1}$, 1084/1085 cm$^{-1}$ and 1095 cm$^{-1}$, to be diagnostic for malignant tumours of non-melanoma type in association with the certain tumour type from other organs than skin with reference to SCC, or a combination of a biomarker and discriminating markers with characteristic spectral parameters at about 1055 cm$^{-1}$, 1071 cm$^{-1}$, 1084/1085 cm$^{-1}$ and 1095 cm$^{-1}$ with characteristic mean peak values at about 1055 cm$^{-1}$ of about 0.30 or within mean numerical variation range of about 0.09-0.44, at about 1071 cm$^{-1}$ of about 0.36, at about 1084/1085 cm$^{-1}$ of about 0.32 or within mean numerical variation range of about 0.16-0.45, at about 1095 cm$^{-1}$ of about 0.22 or within mean numerical variation range of about 0.08-0.36, corresponding to one of the patterned appearances in IR spectra at about 1055 cm$^{-1}$, 1071 cm$^{-1}$, 1084/1085 cm$^{-1}$ and 1095 cm$^{-1}$, or at about 1055 cm, 1084/1085 cm$^{-1}$ and 1095 cm$^{-1}$, or predominantly at about 1055 cm$^{-1}$ and 1084/1085 cm$^{-1}$, to be diagnostic for malignant tumours of non-melanoma type in association with the certain tumour type from other organs than skin with reference to BCC; and (vii) diagnosing said patient with benign tumours in association with the certain tumour type from other organs than skin with reference to MN, or premalignant tumours in association with the certain tumour type from other organs than skin with reference to BD, or malignant tumours of melanoma type in association with MM from other organs than skin with reference to MM in skin, or malignant tumours of non-melanoma type in association with SCC from other organs than skin with reference to SCC in skin, or malignant tumours of non-melanoma type in association with BCC from other organs than skin with reference to BCC in skin, when corresponding spectral pattern of a tumour biomarker molecular expression profile according to step (v) and its associated combination of molecular expression of discriminating markers according to step (vi) in correlation with characteristic measurements of the presence, absence and/or levels of the measured biomarker at about 1055 cm$^{-1}$ and/or the peak(s) at about 1071, 1084/1085 and/or 1095 cm$^{-1}$ in DNA/RNA triad is detected, wherein diagnosing the patient with benign tumours in association with the certain type from other organs than skin tissue with reference to MN in skin when one among 2 MN spectral patterns of said non-constant presence of a biomarker at prevailing left-shifted peak position along with said presence of the peaks at about 1071 cm$^{-1}$ and 1084/1085 cm$^{-1}$ within said mean values and/or intensity ranges, or said non-constant presence of a biomarker at prevailing left-shifted peak position along with said presence of the peak at about 1084/1085 cm$^{-1}$ within said mean values and/or intensity ranges throughout a whole tumourous tissue of a patient is detected, or diagnosing the patient with premalignant tumours in association with the certain type from other organs than skin tissue with reference to BD in skin when one among 2 BD spectral patterns of said non-constant presence of a biomarker at prevailing left-shifted peak position along with 1 peak at about 1084/1085 cm$^{-1}$ within said mean values and/or intensity ranges, or said absence of a biomarker along with 1 peak at about 108411085 cm$^{-1}$ within said mean values and/or intensity ranges throughout a whole tumourous tissue of a patient is detected, or diagnosing the patient with malignant tumours of melanoma type from other organs than skin tissue with reference to MM in skin when one among 3 MM spectral patterns of said constant presence of a biomarker at the most left-shifted peak position along with 3 peaks at about 1071, 1084/1085 and 1095 cm$^{-1}$ within said mean values and/or intensity ranges, or said constant presence of a biomarker at the most left-shifted peak position along with 2 peaks at about 108411085 and 1095 cm$^{-1}$ within said mean values and/or intensity ranges, or said absence of a biomarker along with 1 peak at about 1084/1085 cm$^{-1}$ within said mean values and/or intensity ranges throughout a whole tumourous tissue of a patient is detected, or diagnosing the patient with malignant tumours of non-melanoma type from other organs than skin tissue with reference to SCC in skin when one among 4 said SCC spectral patterns of said constant presence of a biomarker at the right-shifted peak position along with 3 peaks at about 1071, 1084/1085 and 09 cm$^{-1}$ within said mean values and/or intensity ranges, or said constant presence of a biomarker at the right-shifted peak position along with 2 peaks at about 1084/1085 and 1095 cm$^{-1}$ within said mean values and/or intensity ranges, or said constant presence of a biomarker at the right-shifted peak position along with 1 peak at about 1084/1085 cm$^{-1}$ within said mean values and/or intensity ranges, or said absence of a biomarker along with 3 peaks about 1071, 1084/1085 and 1095 cm$^{-1}$ within said mean values and/or intensity ranges throughout a whole tumourous tissue of a patient is detected, or diagnosing the patient with malignant tumours of non-melanoma type from other organs than skin tissue with reference to BCC in skin, when one among 3 said BCC spectral patterns of said constant presence of a biomarker at the most right-shifted peak position along with 3 peaks at about 1071, 1084/1085 and 1095 cm$^{-1}$ within said mean values and/or intensity ranges, or said constant presence of a biomarker at the most right-shifted peak position along with 2 peaks at about 1084/1085 and 1095 cm$^{-1}$ within said mean values and/or intensity ranges, or said constant presence of a biomarker at the most right-shifted peak position along with 1 peak at about 1084/1085 cm$^{-1}$ within said mean values and/or intensity ranges throughout a whole tumourous tissue of a patient is detected.

15. A biomarker, diagnostic for benign, premalignant and malignant skin tumours, with characteristic molecular expression profile with characteristic spectral parameter at consistent and significant absorption wave number at about 1055 cm$^{-1}$, the multiplet characterized by the ratio of 2 spectral bands of nucleic acids corresponding to identity and secondary structures to molecules DNA and RNA in correlation with characteristic measurements of the measured biomarker in a total number of IR spectra, its peak position and/or shift, the peak value and/or its intensity on FTIR spectrometer in the irradiated skin epidermis of a patient, when used for detecting, predicting and prognosing benign, premalignant and malignant skin tumours in a patient, and/or when used for screening and follow-up of epidermal skin cancers and precancers in a patient, which is one selected from:

(i) a nucleic acid molecule with characteristic predominant left-shifted mean peak position of about 1054 cm$^{-1}$ or within mean position variation range of about 1053-1055 cm$^{-1}$ on FTIR spectrometer, with characteristic mean peak values of about 0.20 or within mean numerical variation range of about 0.17-0.24, with characteristic mean peak intensities of about 0.68 or within mean numerical variation range of about 0.59-0.75, and with characteristic predominant non-constant molecular expression throughout a whole pathological skin epidermis identified in a total number of IR spectra, to be diagnostic for benign skin tumours in association with MN; or (ii) a nucleic acid molecule with characteristic left-shifted mean peak position of about 1053 cm$^{-1}$ or within mean position variation range of about 1052-1053 cm$^{-1}$ on FTIR spectrometer, with characteristic mean peak values of about 0.21 or within mean numerical variation range of about 0.15-0.26, with characteristic mean peak intensities of about 0.72 or within mean numerical variation range of about 0.66-0.77, and with characteristic dominant non-constant molecular expression throughout a whole pathological skin epidermis identified in a total number of IR spectra, to be diagnostic for premalignant skin tumours in association with BD; or (iii) a nucleic acid molecule with characteristic predominant most left-shifted mean peak position of about 1052 cm$^{-1}$ or within mean position variation range of about 1050-1054 cm$^{-1}$ on FTIR spectrometer, with characteristic mean peak values of about 0.20 or within mean numerical variation range of about 0.14-0.26, with characteristic mean peak intensities of about 0.58 or within mean numerical variation range of about 0.47-0.69, and with characteristic constant molecular expression throughout a whole pathological skin epidermis identified in a total number of IR spectra, to be diagnostic for malignant skin tumours of melanoma type in association with MM; or (iv) a nucleic acid molecule with characteristic prevailing right-shifted mean peak position of about 1057 cm$^{-1}$ or within mean position variation range of about 1054-1060 cm$^{-1}$ on FTIR spectrometer, with characteristic mean peak values of about 0.36 or within mean numerical variation range of about 0.13-0.66, with characteristic mean peak intensities of about 0.86 or within mean numerical variation range of about 0.77-1.00, and with characteristic constant molecular expression throughout a whole pathological skin epidermis identified in a total number of IR spectra, to be diagnostic for malignant skin tumours of non-melanoma type in association with SCC; or (v) a nucleic acid molecule with characteristic predominant most right-shifted mean peak position of about 1058 cm$^{-1}$ or within mean peak position variation range of about 1053-1062 cm$^{-1}$ on FTIR spectrometer, with characteristic mean peak values of about 0.30 or within mean numerical variation range of about 0.09-0.44, with characteristic mean peak intensities of about 0.83 or within mean numerical variation range of about 0.59-0.96, and with characteristic constant molecular expression throughout a whole pathological skin epidermis identified in a total number of IR spectra, to be diagnostic for malignant skin tumours of non-melanoma type in association with BCC.

* * * * *